United States Patent [19]

Dungan

[11] Patent Number: 5,591,219
[45] Date of Patent: Jan. 7, 1997

[54] FREQUENCY MODULATOR

[76] Inventor: Thomas E. Dungan, 5139 North Rd., North Street, Mich. 48049

[21] Appl. No.: 280,060

[22] Filed: Jul. 25, 1994

Related U.S. Application Data

[63] Continuation-in-part of Ser. No. 847,294, Mar. 6, 1992, abandoned.

[51] Int. Cl.⁶ .................................................. A61B 17/36
[52] U.S. Cl. ................. 607/88; 607/90; 607/94; 607/100; 606/2; 606/3; 606/17; 604/20; 359/350; 359/722; 250/504 H
[58] Field of Search .................... 604/20; 606/2, 606/3, 8, 17; 607/88, 89, 90, 91, 92, 93, 94, 95, 100; 250/493.1, 494.1, 495.1, 504 R, 504 H; 359/350, 722, 723, 885, 355–357, 359

[56] References Cited

U.S. PATENT DOCUMENTS

| | | |
|---|---|---|
| 785,366 | 3/1905 | Machlett . |
| 2,075,696 | 3/1937 | Boerstler .................................. 250/34 |
| 2,085,627 | 6/1937 | Bodnar .................................. 128/396 |
| 2,183,726 | 12/1939 | Sommer et al. ...................... 128/24.1 |
| 2,452,450 | 10/1948 | Fredenburg .............................. 128/399 |
| 2,533,955 | 12/1950 | Pitts .................................... 128/396 |
| 3,712,984 | 1/1973 | Lienhard .................................. 607/92 |
| 4,229,658 | 10/1980 | Gonser .................................. 250/493.1 |
| 4,783,361 | 11/1988 | Ovshinsky et al. .................... 359/722 |
| 4,816,689 | 3/1989 | Cavicchi .............................. 250/493.1 |
| 4,905,690 | 3/1990 | Ohshiro et al. ....................... 128/395 |
| 4,930,504 | 6/1990 | Diamantopoulos et al. ........... 128/395 |
| 5,086,770 | 2/1992 | Prangley .................................. 607/88 |
| 5,292,346 | 3/1994 | Ceravolo .................................. 606/2 |
| 5,344,433 | 9/1994 | Talmore .................................. 607/88 |
| 5,411,797 | 5/1995 | Davanloo et al. ..................... 428/336 |

FOREIGN PATENT DOCUMENTS 2639834  6/1990  France ............................ A61N 1/40

*Primary Examiner*—Sebastiano Passaniti
*Assistant Examiner*—Mark A. Sager
*Attorney, Agent, or Firm*—Weintraub, DuRoss & Brady

[57] ABSTRACT

A radiation device for therapeutic use in the human body allows the application of light waves to an affected area of the body. A bulb, preferrably a xenon bulb, produces light which is passed through a lens module having silicon and carbon granules therein. By applying different lenses to the device, a variation in the wavelengths of light and radiation applied to an area is achieved. The device has a pistol-like housing to allow for controlled application of the radiation.

14 Claims, 3 Drawing Sheets

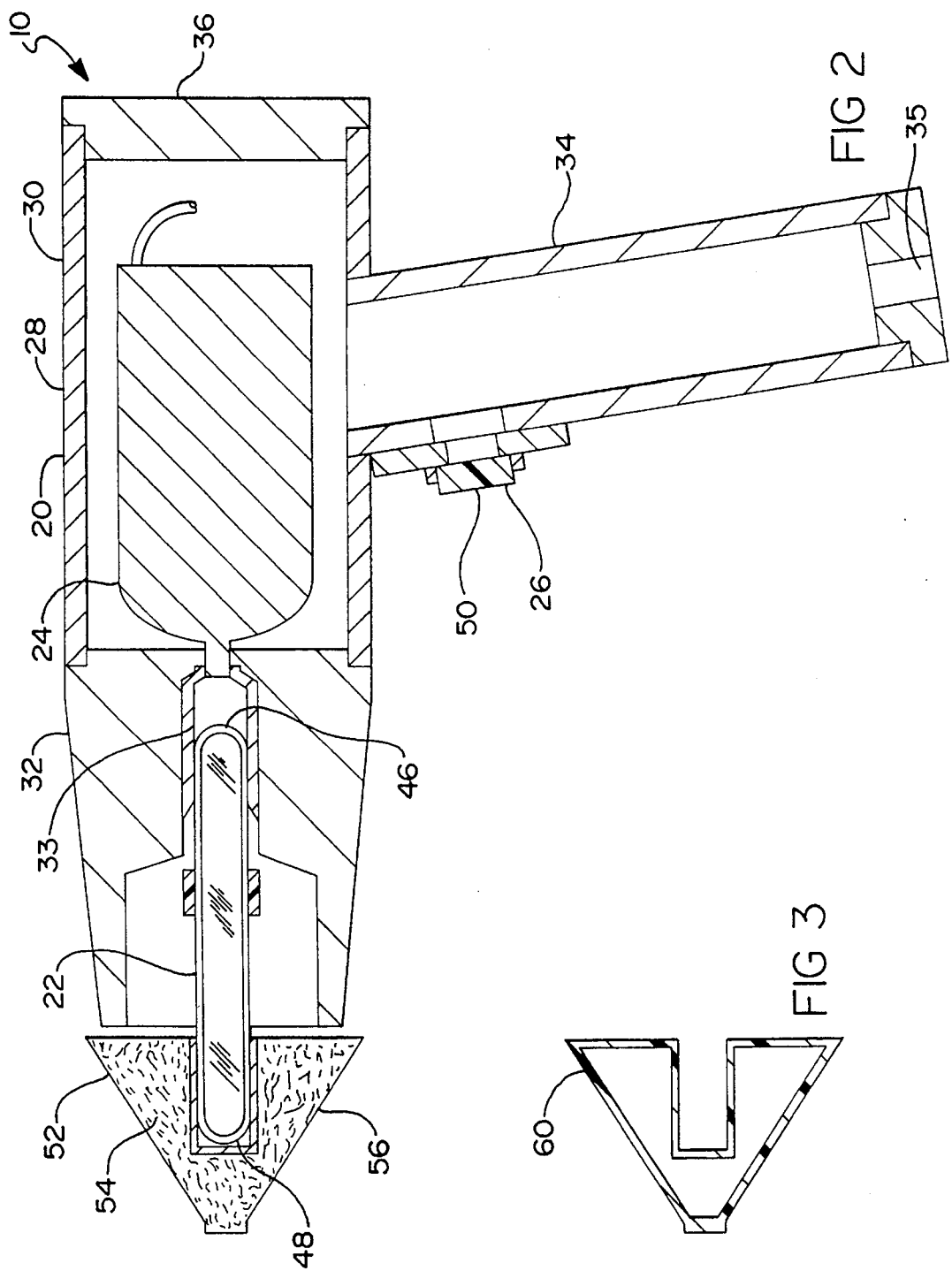

FREQUENCY MODULATOR

BACKGROUND OF THE INVENTION

This application is a continuation-in-part of application Ser. No. 07/847,294, filed Mar. 6, 1992, entitled "Therapeutic Frequency Modulator", which application is herein incorporated by reference, abandoned.

1. Field of the Invention

The present invention concerns therapeutic radiation devices used in the treatment of the human body. More particularly, the present invention concerns therapeutic radiation devices which help effect the reduction of pain and swelling relating to physical trauma incurred by the human body.

2. Description of Prior Art

The use of therapeutic radiation devices to assist in treating physical trauma to the human body is a well known. One therapeutic device, through the application of light rays, treats skin conditions. Examples of such devices are found in U.S. Pat. Nos. 2,183,726 and 3,658,068. In U.S. Pat. No. 2,183,726, issued Dec. 19, 1939 to Sommer et alia and entitled "APPARATUS FOR THE TREATMENT OF THE SKIN OR THE LIKE", the skin treating device thereof utilizes an electric lamp to provide heat and light rays to the skin. The heat and light rays condition the skin to receive skin food or cream which is massaged into the skin by the skin treating device. The light rays from the bulb are filtered through red or blue colored filters. This device is dedicated to skin treatment and does not treat or otherwise address the pain and swelling accompanying trauma to the human body.

U.S. Pat. No. 3,658,068 issued Apr. 25, 1972 to McNall and is entitled "METHOD OF TREATING HYPERBILIRUBINEMIA". McNall teaches is a therapeutic device for treating hyperbilirubinemia, also known as "bilirubin" in newborn infants. This device is a mercury vapor lamp dedicated to treating this one condition. The lamp does not treat any pain or swelling connected with trauma to the human body.

Another type of therapeutic devices are the devices that have direct contact with the human body and use electric current to provide therapeutic benefit to body surfaces. For example, U.S. Pat. No. 785,366, issued Mar. 21, 1905 to Machlett and entitled "VACUUM ELECTRODE", teaches a method of destroying germ organisms by direct contact of the therapeutic device upon the diseased area of the body or skin. This is accomplished by applying electric current through an electrode directly onto the surface of the body. The electrode focuses the current directly to that portion of the diseased skin tissue to be treated thereby destroying microorganisms and germs located at the treatment site. The electric current also aids healthy tissue growth. This electrode does not treat any deep seated traumas, swelling and deep pain, that are present at the site.

Another example, U.S. Pat. No. 2,745,407, issued May 15, 1956 to Mueller et alia and entitled "OZONE THERAPEUTIC DEVICE", is a device which uses a gas tube, charged by an electrode, to charge the environment at or near the diseased skin or tissue area. This device initiates an electric charge which produces a positive ozone environment which changes the oxygen environment surrounding the diseased tissue thereby facilitating healing. There is no teaching in this patent of any treatment of swelling or deep seated pain caused by trauma.

In a further example, U.S. Pat. No. 1,266,287, issued May 14, 1918 TO Longoria and entitled "HIGH FREQUENCY APPARATUS", teaches a high frequency device used for therapeutical treatment of the body. The device discloses an electrode which applies ultraviolet rays directly to the skin surface. Different electrodes are used depending on the area, internal or external, of the body to be treated. Again, the device treats the immediate area of the skin which it touches, but does not affect the deep-seated pain or swelling that may be caused by trauma.

U.S. Pat. No. 4,930,504 issued to Diamantopoulos et alia and is entitled "DEVICE FOR BIOSTIMULATION OF TISSUE AND METHOD FOR TREATMENT OF TISSUE". Diamantopoulos et alia teaches a device of laser light technology to provide therapeutic radiation to treat portions of the body of a patient. The device uses multiple laser diodes to produce infrared and ultraviolet radiation to treat such injuries as inflammations, burns, wounds, ulcers, deficient circulation, pain, nerve degeneration, shingles infections, muscle and ligament damage, arthritis and other types of injuries. This device treats injuries with deep penetrating radiation, but the device must not touch the skin or it could cause surface tissue damage and the device is expensive.

It would be desirable to provide a therapeutic device which filters the energy delivered by a radiating unit to provide treatment to reduce swelling and pain to traumatized portions of the body, which permits contact with the skin and which is relatively inexpensive.

SUMMARY OF THE INVENTION

The therapeutic radiation device of the present invention is used to overcome deep seated swelling and pain from diseases and traumas, as well as surface diseases and trauma of the body. The radiation device comprises:

(a) a housing, the housing comprising:
 (1) a hollow body, the body having a first portion and a second portion; and
 (2) a handle, the handle integrally formed with the body proximate the first portion;

(b) a resonator coil being disposed within the housing;

(c) a radiation source, the radiation source being disposed within the housing, the radiation source having a first end and a second end, the first end of the radiation source being removably connected to the resonator coil, the second end of the radiation source extending beyond the housing, the resonator coil energizing the radiation source, the radiation source emitting a beam of radiation;

(d) an interchangeable lens module, the lens module having a plurality of silicon granules and diamond granules disposed therein, the silicon and diamond granules being attached to each other, the lens module being substantially cone shaped and having a cavity formed therein for attaching onto the radiation source, the lens module being removably connected to the housing;

(e) means for energizing the resonator coil, the means for energizing being electrically connected to the resonator coil; and (f) a transformer, the transformer being electrically connected to the means for energizing, the transformer having a means to regulate the power supplied to the means for energizing.

The silicon and diamond granules cooperate to filter and diffuse the beam of radiation emitted by the radiation source.

The radiation source produces light waves when charged by the resonator coil. The light waves are filtered and diffused by the lens module. The extent of the filtering and diffusion is dependent upon the selection and diffusion of the silicon and diamond granules, and the color of the lens body. The lens is envisioned as being of different colors. Also, the light rays may experience some limited filtering by a lens module not made with silicon and diamond granules.

The amount of radiation to be filtered and diffused is controlled by the transformer. The transformer may have a means for adjustment which can manually or automatically regulate the amount of radiation emitted by the radiation source. Also, the transformer may provide for selection between continuous and remote operation. The transformer is connected to a standard 110 volt power source. When the transformer charges the therapeutic radiation device, radiation produced by the device is then used to treat swelling and pain within the human body.

Various features and advantages and other uses of the present invention will become more apparent by referring to the following detailed description and the drawings in which like reference characters refer to like parts throughout the several views.

BRIEF DESCRIPTION OF THE DRAWINGS

FIG. 2 is a cross-sectional side view of the preferred embodiment of the housing of the present invention;

FIG. 3 is a cross-sectional side view of a second embodiment of the lens module of the present invention.

DESCRIPTION OF THE PREFERRED EMBODIMENTS

Figure 1:
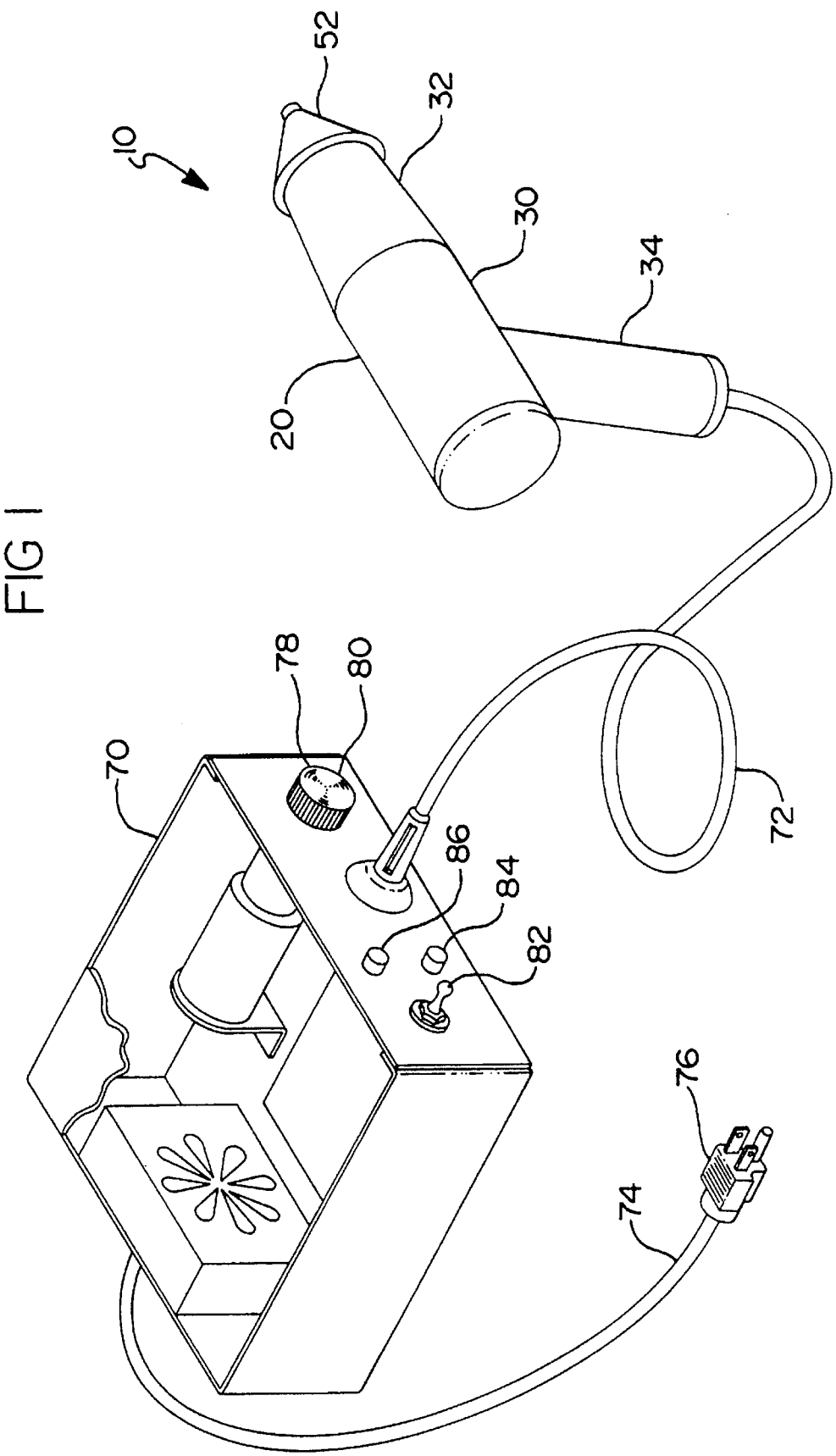
FIG. 1 is a perspective view of the present invention.
Figure 4:
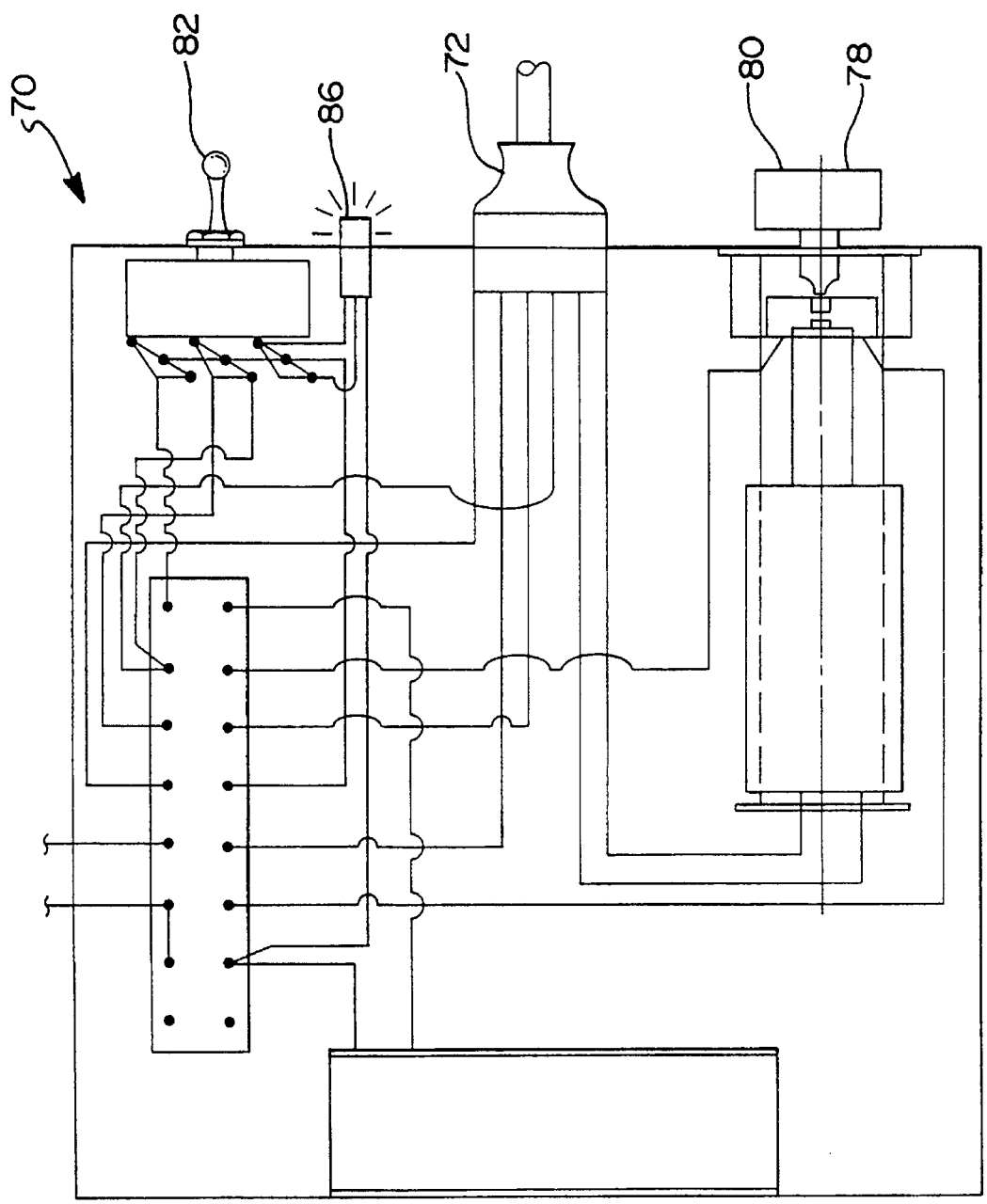
FIG. 4 is a bottom plan view with schematics of the transformer of the present invention.

Referring to the drawings and more particularly to FIGS. 1 and 2, there is depicted therein a first embodiment of the therapeutic radiation device 10 of the present invention. The therapeutic radiation device 10 comprises a housing 20, a radiation source 22 disposed within the housing 20, means 24 for energizing the radiation source 22 and means 26 for engaging the means 24 for energizing the radiation source 22.

The housing 20 comprises a generally cylindrical first portion 30. The first portion 30 has a forward end, a rearward end, a top and a bottom. Formed of plastic or a lightweight metallic alloy, the first poriton 30 is sealed at its rearward end by a cap 36 threadingly engaged thereto. The cap 36 is formed of material similar to the first portion 30.

The housing 20 further comprises a second portion 32 formed materially similarly to the first portion 30. The second portion 32, as depicted in FIGS. 1 and 2, is formed in a truncated conical form, with the forward end having a smaller opening than the rearward end. The second portion 32 is connected, and preferrably threadingly engaged, at the rearward end thereof to the forward end of the first portion 30, in a manner commonly known. The extension of the second portion 32 is formed such that a radiation source 12 such as a bulb may be seated securely therein, as described herein further below.

A handle 34, comprising a generally cylindrical member formed of material similar to the first portion 30, is threadingly attached to the bottom of the first portion 30. An access slot 35 is formed at the base of the handle 34, such that electrical connection means 72 may be fed therethrough, as shown in FIG. 1. In an alternate embodiment, the handle 34 may be unitarily formed to the first portion 30.

The radiation produced by the present device 10 is generated by the interaction of the radiation source 22, the means 24 for energizing the radiation source 22, and the means 26 for engaging the means 24 for energizing. All of the elements 22, 24, 26 are contained within the housing 20, as set forth herein below.

The radiation source 22 comprises, in the preferred embodiment, an elongated light emitting bulb. The bulb 23 22 has a rearward end 46 and a forward end 48. The interior surface 33 of the second portion 32 is formed such that the rearward end 46 of the bulb 23 may be securely seated therein. The forward end of the bulb 23 extends beyond the forward end of the second portion 32 of the housing 20.

The bulb 23 is a gas-filled bulb, preferrably filled with xenon gas. The xenon bulb, when charged, emits a white light that is both a continuous light source and approximates the color spectrum of daylight. Thus, the beam of light produced from a xenon bulb is of the radiation wavelengths of the visible color spectrum, exhibiting strong infrared and nearinfrared radiation between 800 and 1000 nanometers, and demonstrate a large amount of ultraviolet radiation between 250 and 400 nanometers. While the therapeutic effects of light waves of the visible spectrum is undetermined, the therapeutic value of the waves from the infrared and ultraviolet light waves are amply demonstrated, as will be discussed herein further below.

Alternately, other types of bulbs may be used. One such alternative is a vacuum bulb produced and sold by P. J. Supply Co. of Chicago, Ill. The vacuum is not a true vacuum electrode, but is essentially a near vacuum electrode. The clear glass bulb has all the gas removed except for some gas remaining to, when electrically charged, emits a blue light, as is known. The blue light is a narrower color spectrum of the band; thus, it emits a smaller band of infrared rays. Also, other inert or noble gases may be used within the bulb 22. Like the vacuum electrode, the available treatment bands are narrower than xenon gas.

The bulb 23 receives an electrical charge from the means 24 for energizing the radiation source. The means 24 for energizing is, in the preferred embodiment, a resonance coil 38, which is well known. Alternately, the means 24 for energizing may comprise a resonator transformer of the variety known in the art and commonly available. The means 24 for energizing passes a charge into the bulb 23. The resonance transformer is commercially available from Electro-Tech of Chicago, Ill.

The means 26 for engaging the means 24 for energizing the radiation source is disposed within the handle 34. The means 26 for engaging comprises, in the preferred embodiment an electrical switch. The switch comprises a push-button switch 50, however other types of switches, such as a selector switch, may be elected. Such switches are well known and commercially available. The means 26 is connected to the means 24 for energizing and to electrical connection means 72 connected to a transformer, as set forth herein below.

The device 10 is connected to a transformer 70 by electrical connection means 72 means such as an electrical line at the handle 34. The transformer 70 controls the amount of energy received by the radiation device 10. The transformer 70 is connected by a cord 74 having a plug 76 to an electrical outlet, such as a wall outlet, so as to draw a 110 volt current, as is well known. The transformer 70 has means 78 for regulating the power supplied to the device 10, generally comprising a power adjustment switch 80, a preposition selector switch 82, a continuous use light 84 and a remote use light 86. The preposition switch 82 is positioned either in the "off" position, "continuous-use" position, or the "remote-use" position. All of the elements of the transformer 78 are well known and commercially available.

The power adjustment switch 80 permits the power to the radiation device 10 to be adjusted. Preferably, the transformer 78 should be able to provide power from a range of 0 volts to 50,000 volts. Settings between 60 to 70% of this full power have been found to be most effective for most treatments. Since each human being is different in need, the exact settings for treatment for an individual is adjustable to accommodate all needs.

The device 10 further comprises a lens module 52. The lens module 52 is disposed at the forward end of the second portion 32 of the housing 20. The module 52 comprises a mixture of silicon granules and carbon granules, indicated at 54. The silicon granules are, preferably, sand. The carbon granules are, preferably, diamond fragments. The carbon and silicon granules 54 are held together with a clear epoxy adhesive material, as is commonly known and commercially available.

The lens module 52 is, preferably, formed in a conical shape, with the point thereof truncated. This conical shape is preferred as it increases the amount of surface 56 for the body treatments. However, other suitable shapes may be elected, if desired. A channel is formed axially within the module 52, such that the forward end of the bulb 23 may be received therein.

The lens module 52 modulates the wavelength of light being emitted from the radiation source 22. The silicon and carbon granules 54 filter the light. The percentage of frequency modulation may also vary with the type of radiation source 22 used, but the frequency will always be less with a module 52 than without a module 52.

As noted, the lens module 52 may be different colors such as red, white, blue, green, orange, purple, yellow or any other color that would be translucent. The different colors not only alter the frequency of the light waves, but also filter out certain light wave colors. For example, the red module filters a portion of the infrared and near infrared wavelengths and the blue module filters ultraviolet wavelengths.

Referring to FIG. 3, there is shown another embodiment of the lens module 60 made from translucent plastic. However, a translucent glass may also be used. Also, the different colors may be used with the non-silicon lens body module in such a manner as to reduce the harmful effects of light from placing the radiating device 10 close to or upon the surface of the skin tissue of a human body.

Tests have demonstrated that the frequency of the light wave energy emitted by the radiation source is altered by 10% to 30% by the lens module 52 as measured at one-half inch from the module 52.

| MODULE COLOR | MODULATION |
| --- | --- |
| No module | 0% |
| White | 14% less freq. |
| Blue | 28% less freq. |
| Red | 14% less freq. |
| Green | 18% less freq. |
| Orange | 9% less freq. |
| Yellow | 19% less freq. |
| Purple | 7% less freq. |

Which lens module 52, 60 is used, or the color selected for that module, will be dictated by the nature of the injury to be treated. If the injury is on or near the surface of the skin, a lens module 52 that would provide for deep wavelength penetration would not be required. Also, a lens module 52 that would provide for surface absorption only would not be applicable.

In use, the therapeutic radiation device 10 is positioned on or near the area of the body to receive therapeutic treatment. The lens module 52 is placed on or near the skin surface of the traumatized area. The transformer 80 is turned on to either continuous use or remote use. The power supply from the transformer 70 is set by the adjustable switch at the desired setting. When the operator is ready to operate the radiation device 10, the operator pushes the push-button switch 50 on the handle 34 of the device 10. This thereby releases energy through the means for energizing 24, preferably a resonance coil 38 to the radiation source 22. The radiation source 22 illuminates, causing light waves to be directed to the portion of the body which is to be treated. The device 10 hereof reduces swelling of human body parts caused by trauma and diseases and thereby facilitates healing.

Ultraviolet radiation does not penetrate very far into human tissue. Therefore, the effects of the ultraviolet radiation on a human body is generally limited to surface or near surfaces effects such as treating skin diseases; for example, psoriasis, pityriosis rosea, acne and bacteria related to infections. However, there are serious side effects from ultraviolet radiation that must be guarded against, such as sunburn and certain forms of skin cancer.

Infrared radiation, on the other hand, is absorbed by the human body near the surface of the tissue and, in some spectrum ranges (780 to 1400 nm) will penetrate as far as the blood vessels. The deep penetrating infrared radiations are used to therapeutically treat such injuries as sprains, strains, bursitis, peripheral vascular diseases, arthrities, muscle pain and other aches and pains for which the infrared heat can give relief.

The application of heat to the human body skin surface produces effects in the deeper portions of the body, such as muscle relaxation, increased blood supply, and stimulated metabolic activity. Relaxation of the muscle tissue results in relief of pain, improved blood supply and reduced swelling, which all contribute to facilitating the healing process.

As noted, the radiation device 10 may also be used to treat surface or near surface injuries and diseases.

The present invention has been used to treat various conditions in clinical settings. The results of those clinical treatments have been reported by several chiropractic practitioners who have agreed to test the present invention. The results are summarized in the following examples.

EXAMPLE I

A female patient, age 55, complained of swelling in her knee. She demonstrated the swelling by attempting to place her hands around her knee, in an effort to touch her fingers, with no success. The patient was treated with a white lens module for three minutes. The patient experienced immediate reduction in swelling and was able to grip her knee with her hands and touch her fingers.

EXAMPLE II

A male patient, age 28, suffered constant pain from swelling of a broken arm that was confined in a cast. The patient was treated for two minutes with the present invention. The patient experienced immediate reduction of the swelling and pain was relieved.

EXAMPLE III

A male patient, age 38, complained of sinus swelling which interfered with his sleeping. A single treatment with the present invention for one minute relieved the sinus swelling and the accompanying sinus headache.

EXAMPLE IV

A male patient, age 35, complained of an unusual pressure or swelling with pain in his ear. The patient was treated with the present invention for thirty seconds and experienced immediate relief from the pressure and pain.

EXAMPLE V

A female patient, age 52, complained of pain and swelling in her back and left wrist. She also had some apparent skin lacerations. The patient was treated with the present invention for thirty seconds. The patient experienced a reduction of the swelling, relief from pain and reported significant healing of the skin lacerations the next morning.

EXAMPLE VI

A female patient, age greater than 60, suffered from a skin lesion on her ear, which had been described as being possibly cancer. The patient received eight treatments of twenty to thirty seconds which resulted in the lesion disappearing.

EXAMPLE VII

A patient complained of severe sinus headaches. The patient experienced relief after one treatment with the present invention for thirty seconds.

EXAMPLE VIII

A patient experienced severe joint pain for approximately eight years. The patient received two treatments of thirty-second duration, resulting in relief of the pain.

EXAMPLE IX

A lymphectomy performed on a patient induced arm swelling and pain after the operation. Two treatments, within one week of each other, relieved the pain and swelling.

EXAMPLE X

A stroke victim was unable to open and close a hand. The patient received one treatment which resulted in resolution of the problem.

The early indications are that the present invention may be used for various therapeutic purposes. Also, the treatments demonstrate that shorter and fewer treatment periods using the radiation device 10 produce more immediate and greater relief than the longer and greater number of treatment periods demonstrated by the prior art devices.

The instant invention has been described as being used for treatment of swelling and pain as a result of trauma in the human body and skin diseases and lesions. This description is not in any way intended to limit the therapeutic uses for the invention. A person trained in the art of healing may find many therapeutic uses for the radiation device.

Having thus described the present invention, what is claimed is:

1. A therapeutic radiation device comprising:
   (a) a housing, the housing comprising:
      (1) a hollow body, the body having a first portion and a second portion; and
      (2) a handle, the handle integrally formed with the body proximate the first portion;
   (b) a resonator coil, the resonator coil being disposed within the housing;
   (c) a radiation source, the radiation source being disposed within the housing, the radiation source having a first end and a second end, the first end of the radiation source being removably connected to the resonator coil, the second end of the radiation source extending beyond the housing, the radiation source energized by the resonator coil;
   (d) an interchangeable lens module, the lens having a plurality of silicon and diamond granules, the silicon diamond granules being attached to each other, the lens module having a cavity formed therein for enclosing the second end of the radiation source, the lens module being removably attached to the housing;
   (e) means for energizing the resonator coil, the means for energizing being electrically connected to the resonator coil;
   (f) a transformer, the transformer being electrically connected to the means for energizing, the transformer having a means to regulate the power flow to the radiation device; and
   wherein the silicon granules and diamond granules cooperate to filter and diffuse the beam of radiation emitted by the radiation source.

2. The radiation device of claim 1, wherein the means for energizing the device is disposed within the handle of the housing.

3. The radiation device of claim 2, wherein the means for energizing the device comprises:
   (a) a push button switch.

4. The radiation device of claim 1, wherein the means to regulate the power flow comprises:
   (a) a three-position selector switch;
   (b) a continuous use light for when the three-position selector switch is set for continuous use;
   (c) a remote use light for when the three-position selector switch is set for remote use; and
   (d) a power adjustment switch to regulate the amount of electrical energy distributed to the radiation device.

5. The radiation device of claim 4 wherein the lens body is a translucent plastic.

6. A therapeutic radiation device comprising:
   (a) a housing comprising:
      (1) a hollow body having a first portion and a second portion; and
      (2) a handle integrally formed with the body proximate the first portion;
   (b) a resonator coil disposed within the housing;
   (c) a vacuum bulb disposed within the housing, the bulb having a first end and a second end, the first end of the bulb being removably connected to the resonator, the second end of the bulb extending beyond the housing;
   (d) a translucent plastic lens module being essentially cone shaped, the lens module being removably mounted upon the bulb;

(e) means for energizing the resonator coil and the vacuum bulb, the means for energizing being disposed within the handle of the housing, the means for energizing being electrically connected to the resonator coil; and (f) a transformer electrically connected to the means for energizing, the transformer having a means to regulate the power flow to the radiation device, the transformer being removably connected to an electrical outlet.

7. A therapeutic radiation device comprising:

(a) a radiation source generating a beam of radiation;

(b) means for energizing the radiation source;

(c) a lens module mounted onto the radiation source, the lens module comprising a plurality of silicon granules and a plurality of diamond granules, the silicon granules and the diamond granules cooperating to filter and diffuse the beam of radiation.

8. The device of claim 7, further comprising:

a housing having a first portion and a second portion connected thereto, the lens module being mounted to the second portion, the radiation source being at least partially disposed within the second portion, the means for energizing being disposed in the first portion.

9. The device of claim 8, wherein the means for energizing comprises a resonance coil.

10. The device of claim 8, wherein the means for energizing comprises a resonator transformer.

11. The device of claim 9, further comprising:

means for engaging in electrical connection with the resonance coil.

12. The device of claim 7, wherein the radiation source comprises a xenon bulb.

13. The device of claim 11, wherein the means for engaging comprises a switch.

14. The device of claim 11, further comprising: a transformer in electrical connection with the means for engaging.

* * * * *